United States Patent
Li

(10) Patent No.: US 10,261,070 B2
(45) Date of Patent: Apr. 16, 2019

(54) URINE DETECTION METHOD AND URINE DETECTION DEVICE

(71) Applicant: BOE TECHNOLOGY GROUP CO., LTD., Beijing (CN)

(72) Inventor: Hui Li, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 15/207,828

(22) Filed: Jul. 12, 2016

(65) Prior Publication Data
US 2017/0205392 A1 Jul. 20, 2017

(30) Foreign Application Priority Data
Jan. 14, 2016 (CN) .......................... 2016 1 0025201

(51) Int. Cl.
*G01N 27/327* (2006.01)
*G01N 33/493* (2006.01)
(Continued)

(52) U.S. Cl.
CPC .......... *G01N 33/493* (2013.01); *C12Q 1/005* (2013.01); *C12Q 1/006* (2013.01); *C12Q 1/54* (2013.01); *G01N 27/3271* (2013.01)

(58) Field of Classification Search
CPC .......... G01N 27/327–27/3273; G01N 27/333; G01N 33/48493
See application file for complete search history.

(56) References Cited

U.S. PATENT DOCUMENTS 3,857,771 A * 12/1974 Sternberg ........... G01N 27/3271
204/403.05
4,219,530 A * 8/1980 Kopp ..................... G01N 35/00
422/503
(Continued)

FOREIGN PATENT DOCUMENTS

CN 1461347 12/2003
CN 1621845 6/2005
(Continued)

OTHER PUBLICATIONS

"Aim of Statistics in Analytical Chemistry" from Stats Tutorial — Instrumental Analysis and Calibration on the website of the Department of Chemistry, University of Toronto, 2009.*
(Continued)

*Primary Examiner* — Alexander S Noguerola
(74) *Attorney, Agent, or Firm* — Womble Bond Dickinson (US) LLP

(57) ABSTRACT

A urine detection method and a urine detection device are disclosed. Based on types of components to be detected in urine, an equal number of urine samples of a preset volume as the types of components to be detected are selected, wherein each urine sample is used for detecting one component; for each urine sample, based on a component to be detected, the urine sample is mixed with a preset detection object of a fixed mass that can react with the component to be detected in the urine; one or more micro current values of a mixture of the urine sample and the preset detection object within a preset time period are detected; a micro current average value based on the one or more micro current values within the preset time period is calculated; the micro current average value is compared with a pre-established corresponding relationship table of contents of a preset component content and the micro current average values, so as to (Continued)

determine content of the component to be detected in the urine, wherein the preset component is same as the component to be detected.

12 Claims, 3 Drawing Sheets

(51) Int. Cl.
  *C12Q 1/00* (2006.01)
  *C12Q 1/54* (2006.01)

(56) References Cited

U.S. PATENT DOCUMENTS

| | | | |
|---|---|---|---|
| 4,444,644 A * | 4/1984 | Hiramoto | G01N 27/4148 |
| | | | 204/406 |
| 5,198,192 A * | 3/1993 | Saito | A61B 5/14532 |
| | | | 4/314 |
| 2005/0118061 A1 | 6/2005 | Mototsu | |
| 2009/0152131 A1 | 6/2009 | Chang | |
| 2010/0033188 A1 * | 2/2010 | Rieth | A61B 5/01 |
| | | | 324/438 |
| 2011/0189052 A1 * | 8/2011 | Jaeggi | G01N 35/085 |
| | | | 422/68.1 |
| 2013/0245498 A1 * | 9/2013 | Delaney | A61B 5/742 |
| | | | 600/584 |

FOREIGN PATENT DOCUMENTS

| | | |
|---|---|---|
| CN | 101995477 | 3/2011 |
| JP | 2001264320 | 9/2001 |
| WO | WO-2005057210 | 6/2005 |
| WO | WO-2007006180 | 1/2007 |

OTHER PUBLICATIONS

Chinese Office Action with English Language Translation, dated Sep. 27, 2017, Chinese Application No. 201610025201.6.

* cited by examiner

URINE DETECTION METHOD AND URINE DETECTION DEVICE

FIELD

This disclosure relates to the technical field of urine detection, particularly to a urine detection method and a urine detection device.

BACKGROUND

With the improvement of life quality, more and more people begin to focus on their health. In various detections, the urine can reflect multiple body parameters, and urine detection is noninvasive and convenient, hence, urine detection is most widely used. Conventional urine detection generally includes detections of glucose (GLU), bilirubin (BIL), urobilinogen (URO), ketone body (KET), leucocyte (LEC), nitrite (NIT), proteid (PRO), power of hydrogen (pH), occult blood (BLD) and specific gravity (SG) and so on.

At present, the conventional clinic urine detection device includes a dry chemical analyzer and a urine sediment analyzer. The dry chemical analyzer is controlled by a microcomputer, and mainly uses a sphere integrator to receive dual wavelength reflected light for measuring color change of a reagent strip that has reacted with the urine so as to analyze the urine components. The urine sediment analyzer uses the computer to analyze the stained urine for measuring its components. However, the current clinic urine analyzer requires the user to possess certain medical knowledge, thus it is not convenient for use.

SUMMARY

According to a first aspect of this disclosure, a urine detection method is provided, comprising: selecting, based on types of components to be detected in urine, an equal number of urine samples of a preset volume as the types of components to be detected, wherein each urine sample is used for detecting one component; for each urine sample, based on a component to be detected, mixing the urine sample with a preset detection object of a fixed mass that is capable of reacting with the component to be detected in the urine; detecting one or more micro current values of a mixture of the urine sample and the preset detection object within a preset time period; calculating a micro current average value based on the one or more micro current values within the preset time period; comparing the micro current average value with a pre-established corresponding relationship table of contents of a preset component and micro current average values, so as to determine content of the component to be detected in the urine, wherein the preset component is same as the component to be detected.

Optionally, in the detection method, the corresponding relationship table of contents of a preset component and micro current average values is pre-established through the steps of: mixing the preset detection object of the fixed mass with a plurality of urine samples of a preset volume respectively; wherein the content of the preset component in each urine sample has been determined, and the contents in different urine samples are different; detecting one or more micro current values of a mixture of each urine sample and the preset detection object within the preset time period, and calculating a micro current average value based on the one or more micro current values within the preset time period, so as to establish the corresponding relationship table of contents of the preset component and the micro current average values.

Optionally, in the detection method, the preset detection object is enzyme.

Optionally, in the detection method, the preset detection object is glucose oxidase when the component to be detected is glucose.

Optionally, the detection method further comprises: detecting pH value of the urine through an ion-sensitive selective electrode.

According to a second aspect of this disclosure, a urine detection device is further provided, comprising:

at least one first detection container arranged for storing a preset detection object of a fixed mass and urine of a preset volume when detecting a component to be detected in the urine, wherein the preset detection object is capable of reacting with the component to be detected in the urine, and the preset detection objects in different first detection containers are different so as to detect different components in the urine;

a micro current detector arranged for detecting one or more micro current values of a mixture of the urine and the preset detection object in the first detection container within a preset time period, and calculating a micro current average value based on the one or more micro current values within the preset time period, so as to determine content of the component to be detected in the urine based on the micro current average value and a pre-established corresponding relationship table of contents of a preset component and micro current average values, wherein the preset component is same as the component to be detected.

Optionally, the detection device comprises a plurality of first detection containers and a plurality of micro current detectors, wherein the number of the micro current detectors is equal to the number of the first detection containers, and each of the first detection containers corresponds to one micro current detector.

Optionally, the detection device further comprises a plurality of current value converters in one-to-one correspondence with the plurality of micro current detectors, and a display module; wherein, the current value converter is configured to store the pre-established corresponding relationship table of contents of the preset component and the micro current average values, and to compare the micro current average value detected by a micro current detector corresponding to the current value converter with the relationship table, so as to determine content of the component to be detected in the urine;

the display module is configured to display the content of the component to be detected in the urine determined by the current value converter.

Optionally, the detection device comprises a plurality of display modules in one-to-one correspondence with the plurality of current value converters, each of the display modules configured to display the content of the component to be detected in the urine determined by the current value converter corresponding to the each display module.

Optionally, in the detection device, the pre-established corresponding relationship table of contents of the present component and the micro current average values is obtained in the following manners: mixing the preset detection object of the fixed mass with a plurality of urine samples of a preset volume respectively, wherein the content of the preset component in each urine sample has been determined, and the contents in different urine samples are different; detecting one or more micro current values of a mixture of each urine sample and the preset detection object within a preset time period, and calculating a micro current average value based on the one or more micro current values within the preset time period, so as to destablish the corresponding relationship table of contents of the preset component and the micro current average values.

Optionally, the detection device further comprises: a second detection container and an ion-sensitive selective electrode; wherein the second detection container is arranged for storing urine to be detected; the ion-sensitive selective electrode is arranged for detecting pH value of the urine in the second detection container.

Optionally, in the detection device, each of the at least one first detection containers is provided with a volume scale.

Optionally, in the detection device, each of the at least one first detection containers is further provided with a volume alarm; wherein the volume alarm is configured for giving an alarm when a liquid volume in the first detection container exceeds a preset volume threshold.

Optionally, the detection device further comprises: a weighing device arranged for weighing the preset detection object of the fixed mass.

Optionally, the detection device further comprises a fixation rack for fixing the first detection container and the second detection container together.

Optionally, in the detection device, the ion-sensitive selective electrode is arranged for determining pH value of the urine by detecting potential of the urine.

DETAILED DESCRIPTION

Next, the specific implementations of the urine detection method and the urine detection device provided by embodiments of this disclosure will be illustrated in detail with reference to the drawings.

Figure 1:
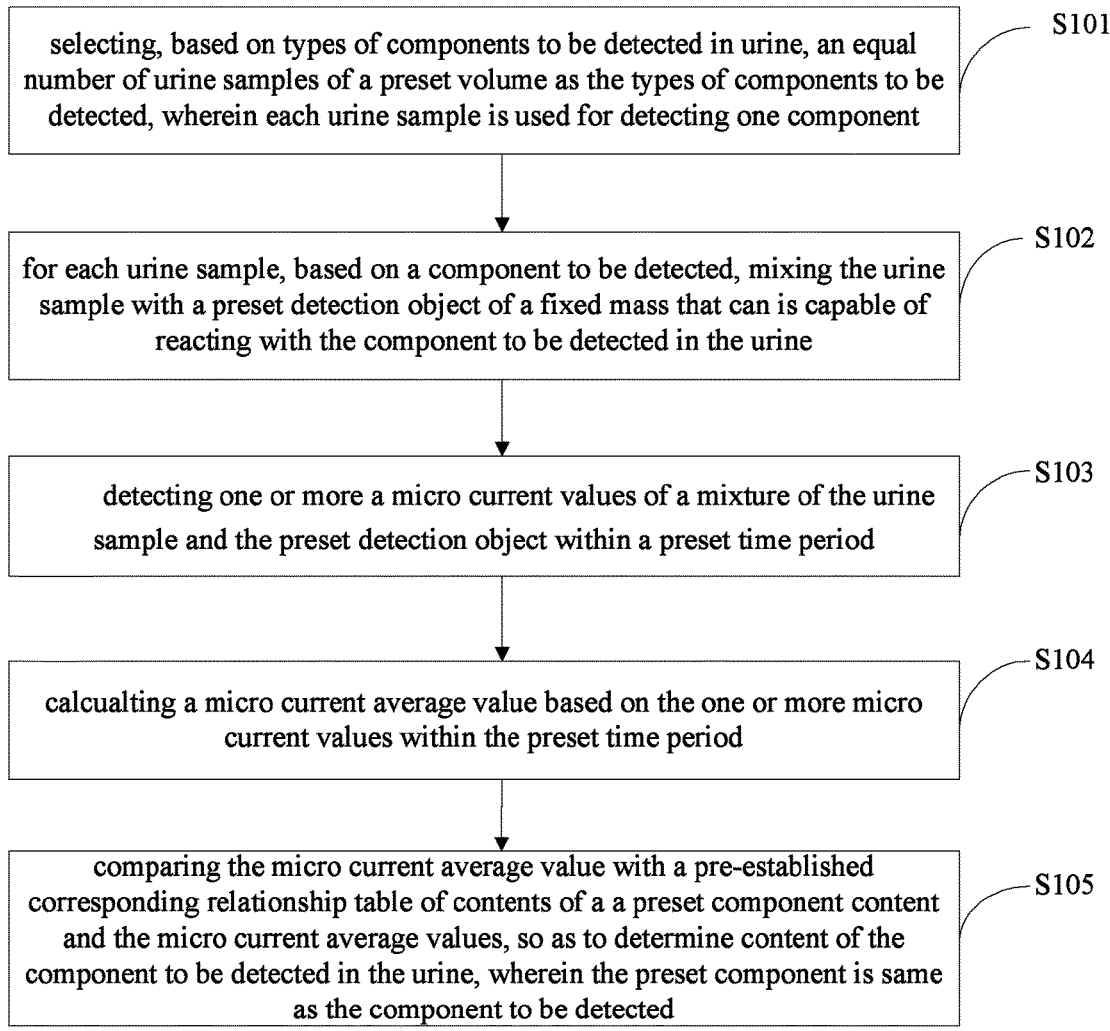
FIG. 1 is a schematic flow chart of a urine detection method according to an embodiment of this disclosure.

FIG. 1 is a schematic flow chart of a urine detection method according to an embodiment of this disclosure. As shown in FIG. 1, the urine detection method comprises the steps of:

S101: selecting, based on types of components to be detected in urine, an equal number of urine samples of a preset volume as the types of components to be detected, wherein each urine sample is used for detecting one component;

S102: for each urine sample, based on a component to be detected, mixing the urine sample with a preset detection object of a fixed mass that can react with the component to be detected in the urine;

S103: detecting one or more micro current values of a mixture of the urine sample and the preset detection object within a preset time period;

S104: calculating a micro current average value based on the one or more micro current values within the preset time period;

S105: comparing the micro current average value with a pre-established corresponding relationship table of contents of a preset component and micro current average values, so as to determine content of the component to be detected in the urine, wherein the preset component is same as the component to be detected.

The urine detection method provided by an embodiment of this disclosure firstly selects, based on the number of the types of components to be detected in urine, an equal number of urine samples of a preset volume as the types of components to be detected, wherein each urine sample is used for detecting one component. Then, for each urine sample, based on a component to be detected, the urine sample is mixed with a preset detection object of a fixed mass that can chemically react with the component to be detected in the urine; and one or more micro current values of a mixture of the urine sample and the preset detection object within a preset time period are detected. Subsequently, a micro current average value can be calculated based on the one or more micro current values within the preset time period. Finally, the micro current average value is compared with a pre-established corresponding relationship table of contents of a preset component and micro current average values, so as to determine content of the component to be detected in the urine, wherein the preset component is same as the component to be detected. In this way, the content of the component to be detected in the urine can be obtained directly, which does not require the user to possess medical knowledge, hence, it is convenient for use.

It should be noted that in the detection method provided by an embodiment of this disclosure, there may be only one component or many types of components to be detected in the urine, which will not be limited here.

Optionally, in the detection method provided by an embodiment of this disclosure, the preset time period generally refers to the reaction time period that the component to be detected in the urine chemically reacts with the preset detection object.

In the detection method provided by an embodiment of this disclosure, the component to be detected can be glucose, bilirubin, urobilinogen, ketone body, leucocyte, nitrite, proteid, hemachrome (for detecting occult blood) and so on in the urine.

As an example, in the detection method provided by an embodiment of this disclosure, a corresponding relationship table of contents of a preset component and micro current average values can be pre-established. The establishment can comprise: mixing the preset detection object of the fixed mass with a plurality of urine samples of a preset volume respectively; wherein the content of the preset component in each urine sample has been determined, and the contents in different urine samples are different; detecting one or more micro current values of a mixture of each urine sample and the preset detection object within the preset time period, and calculating a micro current average value based on the one or more micro current values within the preset time period, so as to establish the corresponding relationship table of contents of the preset component and the micro current average values.

Optionally, in the detection method provided by an embodiment of this disclosure, when each corresponding relationship table of contents of a preset component and micro current average values is established, the preset detection object of the fixed mass and the urine in which the content of the preset component has been determined can be detected for many times, so as to establish the corresponding relationship table of contents of the preset component and the micro current average values based on the results of multiple detection, thereby being capable of reducing errors.

Optionally, in the detection method provided by an embodiment of this disclosure, the preset detection object can be enzyme. Certainly, it can also be other substances that can react with the preset component to be detected in the urine, which will not be defined here.

For example, when the component to be detected is glucose, the preset detection object can be glucose oxidase. Thus, when the urine of a preset volume is mixed with the glucose oxidase, the glucose in the urine reacts with the glucose oxidase to generate hydrogen peroxide, consequently, the content of glucose in the urine can be determined by detecting intensity of the micro current in the mixture.

Optionally, the detection method provided by an embodiment of this disclosure further comprises: detecting pH value of the urine through an ion-sensitive selective electrode. Specifically, the ion-sensitive selective electrode can detect potential of the urine. Because different potentials correspond to different pH values, the pH value of the urine can be determined. The method of testing the pH value of a solution through the ion-sensitive selective electrode is same as the prior art, which will not be repeated here.

Figure 2:
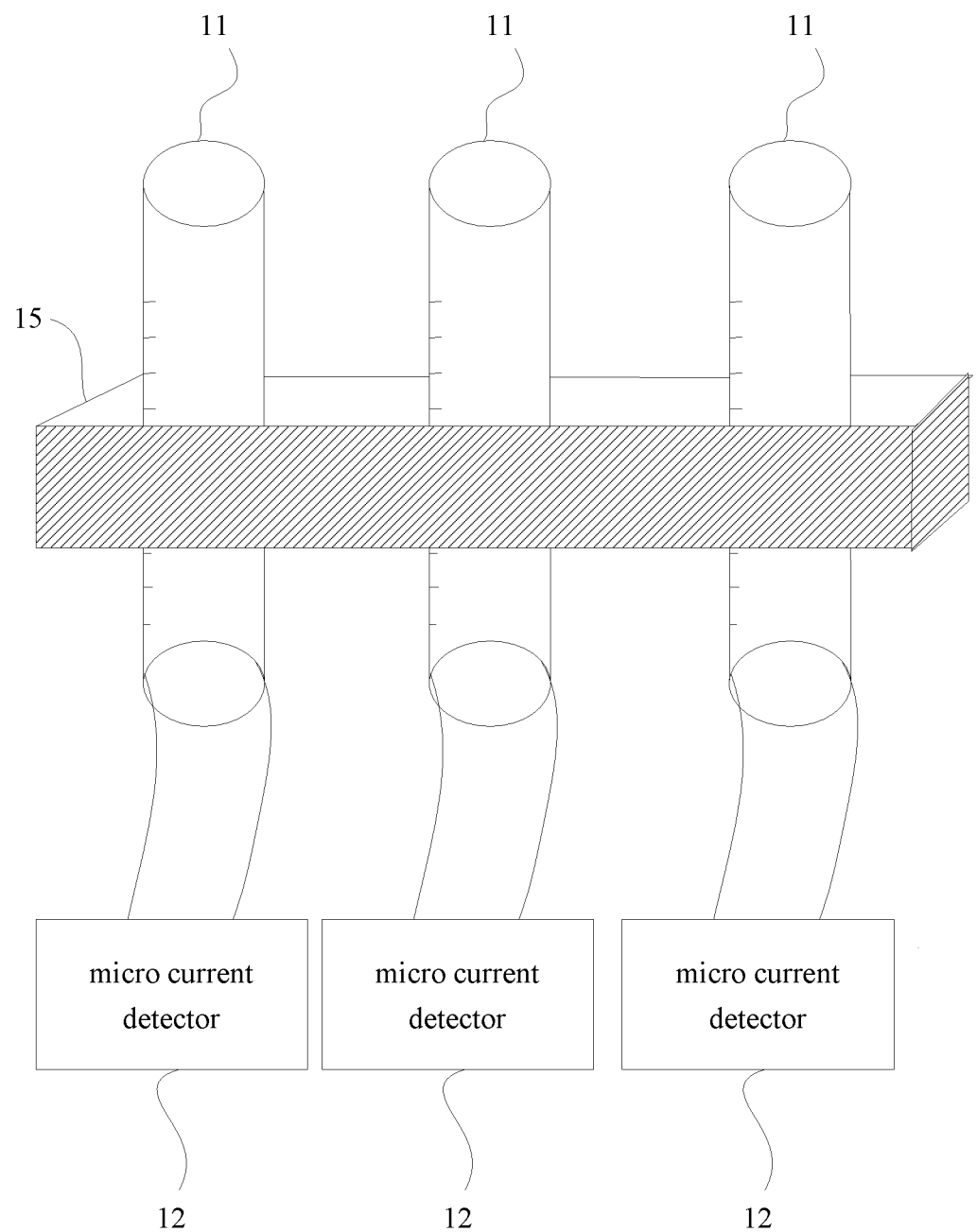
FIG. 2 is a schematic structural diagram of a urine detection device according to an embodiment of this disclosure.

Based on the same inventive concept, an embodiment of this disclosure further provides a urine detection device. FIG. 2 is a schematic structural diagram of a urine detection device according to an embodiment of this disclosure. As shown in FIG. 2, the urine detection device comprises: at least one first detection container 11 (FIG. 2 makes illustration by taking the example of three first detection containers) and at least one micro current detector 12.

The first detection container 11 is arranged for storing a preset detection object of a fixed mass and urine of a preset volume when detecting a component to be detected in the urine, wherein the preset detection object can react with the component to be detected in the urine, and the preset detection objects in different first detection containers are different so as to detect different components in the urine.

The micro current detector 12 is arranged for detecting one or more micro current values of a mixture of the urine and the preset detection object in the first detection container 11 within a preset time period, and calculating a micro current average value based on the one or more micro current values within the preset time period, so as to determine content of the component to be detected in the urine based on the micro current average value and a pre-established corresponding relationship table of contents of a preset component and micro current average values, wherein the preset component is same as the component to be detected.

The micro current detection device provided by an embodiment of this disclosure detects one or more micro current values of a mixture of the urine and the preset detection object in the first detection container within a preset time period through a micro current detector, and calculates a micro current average value based on the one or more micro current values within the preset time period, thereby being capable of obtaining the content of the component to be detected in the urine directly based on the micro current average value and a pre-established corresponding relationship table of contents of a preset component and micro current average values, which does not require the user to possess medical knowledge, hence, it is convenient for use Optionally, as shown in FIG. 2, the detection device provided by an embodiment of this disclosure comprises a plurality of first detection containers 11 and a plurality of micro current detectors 12, wherein the number of the micro current detectors 12 is equal to the number of the first detection containers 11, and each of the first detection containers 11 corresponds to one micro current detector 12. Thus, when a plurality of components have to be detected, they can be detected at the same time, thereby being capable of shortening the detection time. Certainly, in a specific implementation, the detection device can also comprise only one micro current detector, this needs to detect the micro current of the mixture in one first detection container before detecting the micro current of the mixture in the next first detection container, which requires a relatively long detection time.

Optionally, the detection device provided by an embodiment of this disclosure can further comprise a plurality of current value converters and a plurality of display modules, the current value converters are in one-to-one correspondence with the micro current detectors, and the display modules are in one-to-one correspondence with the plurality of current value converters.

The current value converter is configured to store the pre-established corresponding relationship table of contents of the preset component and the micro current average values, and to compare the micro current average value detected by a micro current detector corresponding to the current value converter with the relationship table, so as to determine content of the component to be detected in the urine.

The display module is configured to display the content of the component to be detected in the urine determined by the current value converter corresponding to the display module.

Optionally, the detection device provided by an embodiment of this disclosure comprises one display module. In this way, the determined content of each component to be detected is displayed in the same display module, which is not only convenient for the user to view but also can reduce the cost. Certainly, in a specific implementation, each current value converter can also correspond to one respective display module. Thus, each display module only display the content of one component, which will not be defined here.

Optionally, in the detection device provided by an embodiment of this disclosure, the pre-established corresponding relationship table of contents of the present component and the micro current average values is obtained in the following manners: mixing the preset detection object of the fixed mass with a plurality of urine samples of a preset volume respectively; wherein the content of the preset component in each urine sample has been determined, and the contents in different urine samples are different; detecting one or more micro current values of a mixture of each urine sample and the preset detection object within a preset time period, and calculating a micro current average value based on the one or more micro current values within the preset time period, so as to destablish the corresponding relationship table of contents of the preset component and the micro current average values.

Figure 3:
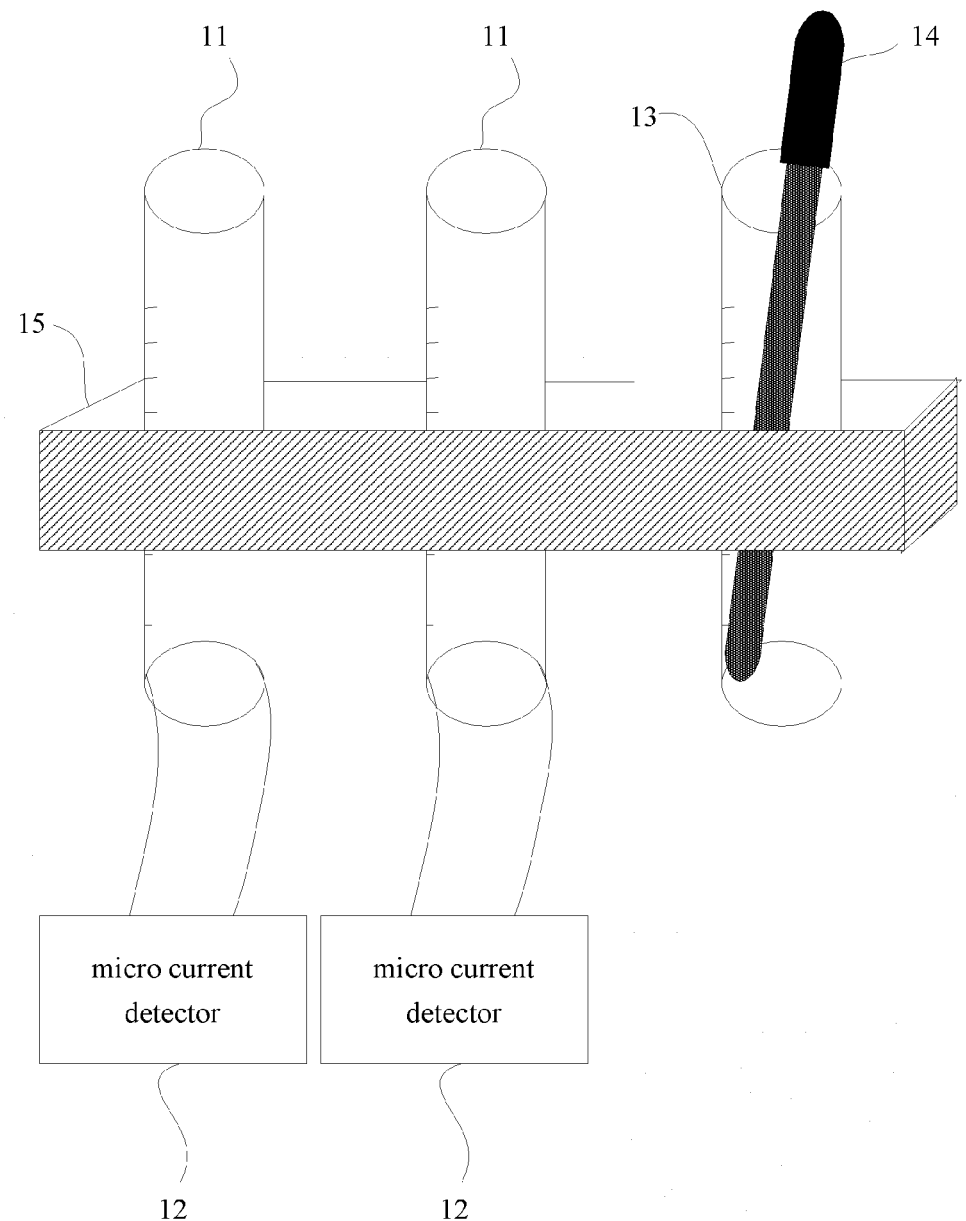
FIG. 3 is another schematic structural diagram of a urine detection device according to an embodiment of this disclosure.

FIG. 3 is another schematic structural diagram of a urine detection device according to an embodiment of this disclosure. As shown in FIG. 3, the detection device provided by an embodiment of this disclosure further comprises: a second detection container 13 and an ion-sensitive selective electrode 14.

The second detection container 13 is arranged for storing the urine to be detected. The ion-sensitive selective electrode 14 is arranged for detecting pH value of the urine in the second detection container 13. In the embodiment, the ion-sensitive selective electrode can determine the pH value of the urine by detecting potential of the urine.

Optionally, in order to pick up the detection device conveniently, as shown in FIG. 2 and FIG. 3, the detection device provided by an embodiment of this disclosure further comprises a fixation rack 15 for fixing all the detection containers together.

Optionally, in the detection device provided by an embodiment of this disclosure, the display module can be further used for displaying the pH value determined by the ion-sensitive selective electrode.

Optionally, in the detection device provided by an embodiment of this disclosure, each of the first detection containers is provided with a volume scale, so as to measure out urine of a preset volume.

Optionally, in the detection device provided by an embodiment of this disclosure, each of the first detection containers is further provided with a volume alarm; wherein the volume alarm is configured for giving an alarm when a liquid volume in the first detection container exceeds a preset volume threshold.

Optionally, the detection device provided by an embodiment of this disclosure further comprises: a weighing device for weighing the preset detection object of the fixed mass.

In the urine detection method and the urine detection device provided by embodiments of this disclosure, firstly, based on types of components to be detected in urine, an equal number of urine samples of a preset volume as the types of components to be detected are selected, wherein each urine sample is used for detecting one component. Then, for each urine sample, based on a component to be detected, the urine sample is mixed with a preset detection object of a fixed mass that can react with the component to be detected in the urine; and one or more micro current values of a mixture of the urine sample and the preset detection object within a preset time period are detected. Subsequently, a micro current average value can be calculated based on the one or more micro current values within the preset time period. Finally, the micro current average value is compared with a pre-established corresponding relationship table of contents of the preset component and the micro current average values, so as to determine content of the component to be detected in the urine, wherein the preset component is same as the component to be detected. In this way, the content of the component to be detected in the urine can be obtained directly, which does not require the user to possess medical knowledge, hence, it is convenient for use.

The skilled person in the art can make various modifications and variations without departing from the spirit and the scope of the present invention. In this way, provided that these modifications and variations of the present invention belong to the scopes of the claims of the present invention and the equivalent technologies thereof, the present invention also intends to encompass these modifications and variations.

The invention claimed is:

1. A urine detection device, comprising:
a plurality of first detection containers and a plurality of micro-current detectors, wherein the number of the micro-current detectors is equal to the number of the first detection containers and each of the first detection containers corresponds to one micro-current detector;
wherein each of the plurality of first detection containers is arranged for storing a preset detection object of a fixed mass and urine of a preset volume when detecting a component to be detected in the urine, wherein the preset detection object is capable of reacting with the component to be detected in the urine, and the preset detection objects in different first detection containers are different so as to detect different components in the urine;
wherein each of the plurality of micro-current detectors is arranged for detecting a plurality of micro-current values of a mixture of the urine and the preset detection object in the corresponding first detection container within a preset time period, and calculating a micro-current average value based on the plurality of micro-current values within the preset time period, so as to determine content of the component to be detected in the urine based on the micro-current average value and a pre-established corresponding relationship table of contents of a preset component and micro-current average values, wherein the preset component is same as the component to be detected, wherein the micro-current average value is an average value of the plurality of micro-current values within the preset time period.

2. The detection device as claimed in claim 1, further comprising: a plurality of current value converters in one-to-one correspondence with the plurality of micro curent detectors, and a display module; wherein,
the current value converter is configured to store the pre-established corresponding relationship table of contents of the preset component and the micro-current average values, and to compare the micro-current average value detected by a micro-current detector corresponding to the current value converter with the relationship table, so as to determine content of the component to be detected in the urine;
the display module is configured to display the content of the component to be detected in the urine determined by the current value converter.

3. The detection device as claimed in claim 2, comprising a plurality of display modules in one-to-one correspondence with the plurality of current value converters, each of the display modules configured to display the content of the component to be detected in the urine determined by the current value converter corresponding to the each display module.

4. The detection device as claimed in claim 1, wherein the pre-established corresponding relationship table of contents of the present component and the micro-current average values is obtained in the following manners:
mixing the preset detection object of the fixed mass with a plurality of urine samples of a preset volume respectively, wherein the content of the preset component in each urine sample has been determined, and the contents in different urine samples are different;
detecting the plurality of micro-current values of a mixture of each urine sample and the preset detection object within a preset time period, and calculating a micro-current average value based on the plurality of micro-current values within the preset time period, so as to establish the corresponding relationship table of contents of the preset component and the micro-current average values.

5. The detection device as claimed in claim 1, further comprising: a second detection container and an ion-sensitive selective electrode; wherein,
the second detection container is arranged for storing urine to be detected;

the ion-sensitive selective electrode is arranged for detecting pH value of the urine in the second detection container.

6. The detection device as claimed in claim 5, further comprising a fixation rack for fixing the first detection container and the second detection container together.

7. The detection device as claimed in claim 5, wherein the ion-sensitive selective electrode is arranged for pH value of the urine by detecting potential of the urine.

8. The detection device as claimed in claim 1, wherein each of the at least one first detection containers is provided with a volume scale.

9. The detection device as claimed in claim 8, wherein each of the at least one first detection containers is further provided with a volume alarm; wherein,
the volume alarm is configured for giving an alarm when a liquid volume in the first detection container exceeds a preset volume threshold.

10. The detection device as claimed in claim 1, further comprising: a weighing device arranged for weighing the preset detection object of the fixed mass.

11. The detection device as claimed in claim 1, wherein the preset detection object is enzyme.

12. The detection device as claimed in claim 11, wherein the preset detection object is glucose oxidase when the component to be detected is glucose.

* * * * *